(12) United States Patent
Hunt

(10) Patent No.: US 8,795,315 B2
(45) Date of Patent: Aug. 5, 2014

(54) EMBOLI CAPTURING DEVICE HAVING A COIL AND METHOD FOR CAPTURING EMBOLI

(75) Inventor: James B. Hunt, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1590 days.

(21) Appl. No.: 11/664,903

(22) PCT Filed: Oct. 6, 2005

(86) PCT No.: PCT/US2005/036164
§ 371 (c)(1),
(2), (4) Date: May 7, 2009

(87) PCT Pub. No.: WO2006/042114
PCT Pub. Date: Apr. 20, 2006

(65) Prior Publication Data
US 2011/0098738 A1  Apr. 28, 2011

Related U.S. Application Data

(60) Provisional application No. 60/616,577, filed on Oct. 6, 2004.

(51) Int. Cl.
*A61M 29/00* (2006.01)
*A61F 2/01* (2006.01)

(52) U.S. Cl.
CPC ......... *A61F 2/013* (2013.01); *A61F 2230/0076* (2013.01); *A61F 2002/018* (2013.01); *A61F 2230/0006* (2013.01); *A61F 2230/008* (2013.01)
USPC ............ 606/200; 604/104; 604/105; 604/106

(58) Field of Classification Search
USPC ................. 606/200, 110–114, 127, 128, 159; 604/104–106
See application file for complete search history.

(56) References Cited

U.S. PATENT DOCUMENTS

| 3,108,593 A | 10/1963 | Glassman |
| 3,334,629 A | 8/1967 | Cohn |
| 3,472,230 A | 10/1969 | Fogarty |

(Continued)

FOREIGN PATENT DOCUMENTS

| DE | 3429850 A1 | 2/1986 |
| EP | 0 865 772 A1 | 9/1998 |

(Continued)

OTHER PUBLICATIONS

International Search Report—PCT/US2005/036164—mailed Jan. 29, 2007.

(Continued)

*Primary Examiner* — Darwin Erezo
*Assistant Examiner* — Katrina Stransky
(74) *Attorney, Agent, or Firm* — Brinks Gilson & Lione

(57) ABSTRACT

An embolic capturing device for capturing emboli within a body lumen is disclosed. The embolic capturing device (10) comprises a filtering basket (20) and at least one coil (22) attached to the basket. The filtering basket includes a frame (23) and a filtering body (30) disposed on the frame. The at least one coil is attached to the filtering body for filtering emboli in the body lumen.

20 Claims, 5 Drawing Sheets

(56) References Cited

U.S. PATENT DOCUMENTS

| | | |
|---|---|---|
| 3,547,103 A | 12/1970 | Cook |
| 3,635,223 A | 1/1972 | Klieman |
| 3,923,065 A | 12/1975 | Nozick et al. |
| 3,952,747 A | 4/1976 | Kimmell, Jr. |
| 3,978,863 A | 9/1976 | Fettel et al. |
| 3,996,938 A | 12/1976 | Clark, III |
| 4,425,908 A | 1/1984 | Simon |
| 4,456,000 A | 6/1984 | Schjeldahl et al. |
| 4,494,531 A | 1/1985 | Gianturco |
| 4,548,206 A | 10/1985 | Osborne |
| 4,561,439 A | 12/1985 | Bishop et al. |
| 4,562,039 A | 12/1985 | Koehler |
| 4,604,094 A | 8/1986 | Shook |
| 4,619,246 A | 10/1986 | Molgaard-Nielsen et al. |
| 4,643,184 A | 2/1987 | Mobin-Uddin |
| 4,646,736 A | 3/1987 | Auth |
| 4,650,472 A | 3/1987 | Bates |
| 4,665,906 A | 5/1987 | Jervis |
| 4,669,464 A | 6/1987 | Sulepov |
| 4,688,553 A | 8/1987 | Metals |
| 4,723,549 A | 2/1988 | Wholey et al. |
| 4,727,873 A | 3/1988 | Mobin-Uddin |
| 4,732,152 A | 3/1988 | Wallsten et al. |
| 4,817,600 A | 4/1989 | Herms et al. |
| 4,824,435 A | 4/1989 | Giesy et al. |
| 4,832,055 A | 5/1989 | Palestrant |
| 4,846,794 A | 7/1989 | Hertzer |
| 4,848,343 A | 7/1989 | Wallsten et al. |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 4,998,916 A | 3/1991 | Hammerslag et al. |
| 5,053,008 A | 10/1991 | Bajaj |
| 5,059,205 A | 10/1991 | El-Nounou et al. |
| 5,069,226 A | 12/1991 | Yamauchi et al. |
| 5,078,726 A | 1/1992 | Kreamer |
| 5,100,423 A * | 3/1992 | Fearnot .................. 606/159 |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,163,927 A | 11/1992 | Woker et al. |
| 5,203,772 A | 4/1993 | Hammerslag et al. |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,397 A | 9/1994 | Palermo et al. |
| 5,350,398 A | 9/1994 | Pavcnik et al. |
| 5,364,345 A | 11/1994 | Lowery et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,451,233 A | 9/1995 | Yock |
| 5,458,573 A | 10/1995 | Summers |
| 5,522,881 A | 6/1996 | Lentz |
| 5,527,338 A | 6/1996 | Purdy |
| 5,531,788 A | 7/1996 | Dibie et al. |
| 5,549,551 A | 8/1996 | Peacock et al. |
| 5,549,626 A | 8/1996 | Miller et al. |
| 5,556,414 A | 9/1996 | Turi |
| 5,562,698 A | 10/1996 | Parker |
| 5,571,135 A | 11/1996 | Fraser et al. |
| 5,591,195 A | 1/1997 | Taheri et al. |
| 5,601,595 A | 2/1997 | Smith |
| 5,624,461 A | 4/1997 | Mariant |
| 5,626,605 A | 5/1997 | Irie et al. |
| 5,630,797 A | 5/1997 | Diedrich et al. |
| 5,634,942 A | 6/1997 | Chevillon et al. |
| 5,649,953 A | 7/1997 | Lefebvre |
| 5,662,703 A | 9/1997 | Yurek et al. |
| 5,669,933 A | 9/1997 | Simon et al. |
| 5,681,347 A | 10/1997 | Cathcart et al. |
| 5,690,642 A | 11/1997 | Osborne et al. |
| 5,690,667 A | 11/1997 | Gia |
| 5,693,067 A | 12/1997 | Purdy |
| 5,693,087 A | 12/1997 | Parodi |
| 5,695,518 A | 12/1997 | Laerum |
| 5,695,519 A | 12/1997 | Summers et al. |
| 5,700,253 A | 12/1997 | Parker |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,738,667 A | 4/1998 | Solar |
| 5,746,767 A | 5/1998 | Smith |
| 5,755,772 A | 5/1998 | Evans et al. |
| 5,755,790 A | 5/1998 | Chevillon et al. |
| 5,766,203 A | 6/1998 | Imran et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,027 A | 9/1998 | Hassett et al. |
| 5,814,064 A | 9/1998 | Daniel et al. |
| 5,820,592 A | 10/1998 | Hammerslag |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,702 A | 6/1999 | Romley et al. |
| 5,911,704 A | 6/1999 | Humes |
| 5,911,717 A | 6/1999 | Jacobsen et al. |
| 5,911,734 A * | 6/1999 | Tsugita et al. .................. 606/200 |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chine et al. |
| 5,928,261 A | 7/1999 | Ruiz |
| 5,938,683 A | 8/1999 | Lefebvre |
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,984,965 A | 11/1999 | Knapp et al. |
| 5,989,281 A | 11/1999 | Barbut et al. |
| 6,001,118 A | 12/1999 | Daniel et al. |
| 6,007,557 A | 12/1999 | Ambrisco et al. |

(56) References Cited

U.S. PATENT DOCUMENTS

| | | | |
|---|---|---|---|
| 6,007,558 A | 12/1999 | Ravenscloth et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,745 A | 5/2000 | Gelbfish |
| 6,059,813 A | 5/2000 | Vrba et al. |
| 6,059,814 A | 5/2000 | Ladd |
| 6,063,104 A * | 5/2000 | Villar et al. ............... 606/213 |
| 6,063,113 A | 5/2000 | Kavteladze et al. |
| 6,066,149 A | 5/2000 | Samson et al. |
| 6,066,158 A | 5/2000 | Engelson et al. |
| 6,068,645 A | 5/2000 | Tu |
| 6,074,357 A | 6/2000 | Kaganov et al. |
| 6,077,274 A | 6/2000 | Ouchi et al. |
| 6,080,178 A | 6/2000 | Meglin |
| 6,083,239 A | 7/2000 | Addis |
| 6,086,577 A | 7/2000 | Ken et al. |
| 6,086,605 A | 7/2000 | Barbut et al. |
| 6,093,199 A | 7/2000 | Brown et al. |
| 6,096,053 A | 8/2000 | Bates |
| 6,096,070 A | 8/2000 | Ragheb et al. |
| 6,099,549 A | 8/2000 | Bosma et al. |
| 6,106,497 A | 8/2000 | Wang |
| 6,126,672 A | 10/2000 | Berryman et al. |
| 6,126,673 A | 10/2000 | Kim et al. |
| 6,129,739 A | 10/2000 | Khosravi |
| 6,136,016 A | 10/2000 | Barbut et al. |
| 6,146,396 A | 11/2000 | Konya et al. |
| 6,146,404 A | 11/2000 | Kim et al. |
| 6,152,931 A | 11/2000 | Nadal et al. |
| 6,152,946 A | 11/2000 | Broome et al. |
| 6,152,947 A | 11/2000 | Ambrisco et al. |
| 6,156,061 A | 12/2000 | Wallace et al. |
| 6,156,062 A | 12/2000 | McGuinness |
| 6,159,230 A | 12/2000 | Samuels |
| 6,165,179 A | 12/2000 | Cathcart et al. |
| 6,165,198 A | 12/2000 | McGurk et al. |
| 6,165,199 A | 12/2000 | Barbut |
| 6,165,200 A | 12/2000 | Tsugita et al. |
| 6,168,579 B1 | 1/2001 | Tsugita et al. |
| 6,168,603 B1 | 1/2001 | Leslie et al. |
| 6,168,610 B1 | 1/2001 | Marin et al. |
| 6,168,622 B1 | 1/2001 | Mazzocchi |
| 6,171,327 B1 | 1/2001 | Daniel et al. |
| 6,171,328 B1 | 1/2001 | Addis |
| 6,174,318 B1 | 1/2001 | Bates et al. |
| 6,179,851 B1 | 1/2001 | Barbut et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,193,739 B1 | 2/2001 | Chevillon et al. |
| 6,203,561 B1 | 3/2001 | Ramee et al. |
| 6,206,931 B1 | 3/2001 | Cook et al. |
| 6,214,025 B1 | 4/2001 | Thistle et al. |
| 6,214,026 B1 | 4/2001 | Lepak et al. |
| 6,221,091 B1 | 4/2001 | Khosravi |
| 6,224,620 B1 | 5/2001 | Maahs |
| 6,231,588 B1 | 5/2001 | Zadno-Azizi |
| 6,231,589 B1 | 5/2001 | Wessman et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,087 B1 | 6/2001 | Addis |
| 6,245,088 B1 | 6/2001 | Lowery |
| 6,245,089 B1 | 6/2001 | Daniel et al. |
| 6,251,092 B1 | 6/2001 | Qin et al. |
| 6,251,122 B1 | 6/2001 | Tsukernik |
| 6,254,550 B1 | 7/2001 | McNamara et al. |
| 6,254,633 B1 | 7/2001 | Pinchuk et al. |
| 6,258,026 B1 | 7/2001 | Ravenscroft et al. |
| 6,258,115 B1 | 7/2001 | Dubrul |
| 6,258,120 B1 | 7/2001 | McKenzie et al. |
| 6,261,305 B1 | 7/2001 | Marotta et al. |
| 6,264,672 B1 | 7/2001 | Fisher |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,277,125 B1 | 8/2001 | Barry et al. |
| 6,277,126 B1 | 8/2001 | Barry et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,710 B1 | 9/2001 | Cryer et al. |
| 6,299,604 B1 | 10/2001 | Ragheb et al. |
| 6,306,163 B1 | 10/2001 | Fitz |
| 6,309,399 B1 | 10/2001 | Barbut et al. |
| 6,312,444 B1 | 11/2001 | Barbut |
| 6,319,268 B1 | 11/2001 | Ambrisco et al. |
| 6,325,815 B1 | 12/2001 | Kusleika et al. |
| 6,325,816 B1 | 12/2001 | Fulton, III et al. |
| 6,328,755 B1 | 12/2001 | Marshall |
| 6,331,183 B1 | 12/2001 | Suon |
| 6,331,184 B1 | 12/2001 | Abrams |
| 6,334,864 B1 | 1/2002 | Amplatz et al. |
| 6,336,934 B1 | 1/2002 | Gilson et al. |
| 6,338,739 B1 | 1/2002 | Datta et al. |
| 6,340,364 B2 | 1/2002 | Kanesaka |
| 6,342,062 B1 | 1/2002 | Suon et al. |
| 6,342,063 B1 | 1/2002 | DeVries et al. |
| 6,344,048 B1 | 2/2002 | Chin et al. |
| 6,344,049 B1 | 2/2002 | Levinson et al. |
| 6,346,116 B1 | 2/2002 | Brooks et al. |
| 6,348,041 B1 | 2/2002 | Klint |
| 6,348,063 B1 | 2/2002 | Yassour et al. |
| 6,350,271 B1 | 2/2002 | Kurz et al. |
| 6,355,051 B1 | 3/2002 | Sisskind et al. |
| 6,358,228 B1 | 3/2002 | Tubman et al. |
| 6,361,545 B1 | 3/2002 | Macoviak et al. |
| 6,361,546 B1 | 3/2002 | Khosravi |
| 6,361,547 B1 | 3/2002 | Hieshima |
| 6,364,895 B1 | 4/2002 | Greenhalgh |
| 6,364,896 B1 | 4/2002 | Addis |
| 6,368,338 B1 | 4/2002 | Konya et al. |
| 6,371,961 B1 | 4/2002 | Osborne et al. |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,379,374 B1 | 4/2002 | Hieshima et al. |
| 6,380,457 B1 | 4/2002 | Yurek et al. |
| 6,383,146 B1 | 5/2002 | Klint |
| 6,383,171 B1 | 5/2002 | Gifford et al. |
| 6,383,174 B1 * | 5/2002 | Eder ............... 606/1 |
| 6,383,193 B1 | 5/2002 | Cathcart et al. |
| 6,383,196 B1 | 5/2002 | Leslie et al. |
| 6,383,205 B1 | 5/2002 | Samson et al. |
| 6,383,206 B1 | 5/2002 | Gillick et al. |
| 6,391,044 B1 | 5/2002 | Yadav et al. |
| 6,391,045 B1 | 5/2002 | Kim et al. |
| 6,391,052 B2 | 5/2002 | Buirge et al. |
| 6,395,014 B1 | 5/2002 | Macoviak et al. |
| 6,402,771 B1 | 6/2002 | Palmer et al. |
| 6,402,772 B1 | 6/2002 | Amplatz et al. |
| 6,409,742 B1 | 6/2002 | Fulton, III et al. |
| 6,413,235 B1 | 7/2002 | Parodi |
| 6,416,530 B2 | 7/2002 | DeVries et al. |
| 6,419,686 B1 | 7/2002 | McLeod et al. |
| 6,423,052 B1 | 7/2002 | Escano |
| 6,423,086 B1 | 7/2002 | Barbut et al. |
| 6,425,909 B1 | 7/2002 | Dieck et al. |
| 6,428,557 B1 | 8/2002 | Hilaire |
| 6,428,558 B1 | 8/2002 | Jones et al. |
| 6,428,559 B1 | 8/2002 | Johnson |

(56) References Cited

U.S. PATENT DOCUMENTS

| | | |
|---|---|---|
| 6,432,122 B1 | 8/2002 | Gilson et al. |
| 6,436,112 B2 | 8/2002 | Wensel et al. |
| 6,436,120 B1 | 8/2002 | Meglin |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,447,531 B1 | 9/2002 | Amplatz |
| 6,454,775 B1 | 9/2002 | Demarais et al. |
| 6,458,139 B1 | 10/2002 | Palmer et al. |
| 6,458,145 B1 | 10/2002 | Ravenscroft et al. |
| 6,461,370 B1 | 10/2002 | Gray et al. |
| 6,468,290 B1 | 10/2002 | Weldon et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,500 B1 | 11/2002 | Kokish et al. |
| 6,485,501 B1 | 11/2002 | Green |
| 6,485,502 B2 | 11/2002 | Don Michael et al. |
| 6,491,712 B1 | 12/2002 | O'Connor |
| 6,494,895 B2 | 12/2002 | Addis |
| 6,497,709 B1 | 12/2002 | Heath |
| 6,499,487 B1 | 12/2002 | McKenzie et al. |
| 6,500,166 B1 | 12/2002 | Zadno Azizi et al. |
| 6,500,191 B2 | 12/2002 | Addis |
| 6,502,606 B2 | 1/2003 | Klint |
| 6,506,203 B1 | 1/2003 | Boyle et al. |
| 6,506,205 B2 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,520,983 B1 | 2/2003 | Colgan et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Klint |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,595,983 B2 | 7/2003 | Voda |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 | 2/2004 | Boyle et al. |
| 6,695,865 B2 * | 2/2004 | Boyle et al. ............ 606/200 |
| 6,702,834 B1 * | 3/2004 | Boylan et al. ............ 606/200 |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,855 B2 | 6/2004 | Yurek et al. |
| 6,755,856 B2 | 6/2004 | Fierens et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 | 8/2004 | Kusleika et al. |

(56) References Cited

U.S. PATENT DOCUMENTS

| | | |
|---|---|---|
| 6,774,278 B1 | 8/2004 | Ragheb et al. |
| 6,780,175 B1 | 8/2004 | Sachdeva et al. |
| 6,793,667 B2 | 9/2004 | Hebert et al. |
| 6,793,668 B1 | 9/2004 | Fisher |
| 6,833,002 B2 | 12/2004 | Stack et al. |
| 6,855,154 B2 | 2/2005 | Abdel-Gawwad |
| 6,866,677 B2 | 3/2005 | Douk et al. |
| 6,866,680 B2 | 3/2005 | Yassour et al. |
| 6,872,211 B2 | 3/2005 | White et al. |
| 6,896,691 B2 | 5/2005 | Boylan et al. |
| 6,929,709 B2 | 8/2005 | Smith |
| 6,932,831 B2 | 8/2005 | Forber |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,469 B2* | 12/2005 | Broome et al. ............... 606/200 |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,128,073 B1 | 10/2006 | Van Der Burg et al. |
| 7,166,120 B2 | 1/2007 | Kusleika |
| 7,189,249 B2 | 3/2007 | Hart et al. |
| 7,255,687 B2 | 8/2007 | Huang et al. |
| 7,285,130 B2 | 10/2007 | Austin |
| 7,306,619 B1 | 12/2007 | Palmer |
| 7,371,248 B2 | 5/2008 | Dapolito et al. |
| 7,393,358 B2 | 7/2008 | Malewicz |
| 7,604,649 B2* | 10/2009 | McGuckin et al. ........... 606/200 |
| 7,666,216 B2 | 2/2010 | Hogendijk et al. |
| 7,731,722 B2 | 6/2010 | Lavelle et al. |
| 7,766,934 B2 | 8/2010 | Pal et al. |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0041928 A1 | 11/2001 | Pavcnik et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002383 A1 | 1/2002 | Sepetka et al. |
| 2002/0002384 A1 | 1/2002 | Gilson et al. |
| 2002/0004667 A1 | 1/2002 | Adams et al. |
| 2002/0010487 A1* | 1/2002 | Evans et al. .................. 606/180 |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099405 A1 | 7/2002 | Yurek et al. |
| 2002/0099407 A1 | 7/2002 | Becker et al. |
| 2002/0099435 A1 | 7/2002 | Stinson |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1* | 9/2002 | Broome et al. ............... 606/200 |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151926 A1 | 10/2002 | Wallace et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0165598 A1 | 11/2002 | Wahr et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0177899 A1 | 11/2002 | Eum et al. |
| 2002/0183781 A1 | 12/2002 | Casey et al. |
| 2002/0183782 A1 | 12/2002 | Tsugita et al. |
| 2002/0183783 A1 | 12/2002 | Shadduck |

(56) References Cited

U.S. PATENT DOCUMENTS

| | | |
|---|---|---|
| 2002/0188313 A1 | 12/2002 | Johnson et al. |
| 2002/0188314 A1 | 12/2002 | Anderson et al. |
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |
| 2003/0004536 A1 | 1/2003 | Boylan et al. |
| 2003/0004537 A1 | 1/2003 | Boyle et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004541 A1 | 1/2003 | Wensel et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucck |
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1 | 3/2003 | Harrison et al. |
| 2003/0050662 A1 | 3/2003 | Don Michael |
| 2003/0055452 A1 | 3/2003 | Joergensen et al. |
| 2003/0055480 A1 | 3/2003 | Fischell et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0065355 A1 | 4/2003 | Weber |
| 2003/0065356 A1 | 4/2003 | Tsugita et al. |
| 2003/0069596 A1 | 4/2003 | Eskuri |
| 2003/0073979 A1 | 4/2003 | Naimark et al. |
| 2003/0074019 A1 | 4/2003 | Gray et al. |
| 2003/0078614 A1 | 4/2003 | Salahieh et al. |
| 2003/0083608 A1 | 5/2003 | Evans et al. |
| 2003/0083692 A1 | 5/2003 | Vrba et al. |
| 2003/0083693 A1 | 5/2003 | Daniel et al. |
| 2003/0088211 A1 | 5/2003 | Anderson et al. |
| 2003/0088266 A1 | 5/2003 | Bowlin |
| 2003/0093110 A1 | 5/2003 | Vale |
| 2003/0093112 A1 | 5/2003 | Addis |
| 2003/0097094 A1 | 5/2003 | Ouriel et al. |
| 2003/0097145 A1 | 5/2003 | Goldberg et al. |
| 2003/0100917 A1 | 5/2003 | Boyle et al. |
| 2003/0100918 A1 | 5/2003 | Duane |
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0109916 A1 | 6/2003 | Don Michael |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 | 7/2003 | Levinson et al. |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171739 A1* | 9/2003 | Murphy et al. .................. 606/1 |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171800 A1 | 9/2003 | Bicek et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212431 A1 | 11/2003 | Brady et al. |
| 2003/0212432 A1 | 11/2003 | Khairkhahan et al. |
| 2003/0212433 A1 | 11/2003 | Ambrisco et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225418 A1 | 12/2003 | Esksuri et al. |
| 2003/0225435 A1 | 12/2003 | Hunter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006365 A1 | 1/2004 | Brady et al. |
| 2004/0006370 A1 | 1/2004 | Tsugita |
| 2004/0015152 A1 | 1/2004 | Day |
| 2004/0039412 A1 | 2/2004 | Isshiki et al. |

(56) References Cited

U.S. PATENT DOCUMENTS

| | | |
|---|---|---|
| 2004/0049226 A1 | 3/2004 | Keegan et al. |
| 2004/0054394 A1 | 3/2004 | Lee |
| 2004/0054395 A1 | 3/2004 | Lee et al. |
| 2004/0059372 A1 | 3/2004 | Tsugita |
| 2004/0064067 A1 | 4/2004 | Ward |
| 2004/0064179 A1 | 4/2004 | Linder et al. |
| 2004/0068271 A1 | 4/2004 | McAlister |
| 2004/0078044 A1 | 4/2004 | Kear |
| 2004/0082962 A1 | 4/2004 | Demarais et al. |
| 2004/0088038 A1 | 5/2004 | Dehnad et al. |
| 2004/0093009 A1* | 5/2004 | Denison et al. .............. 606/200 |
| 2004/0093012 A1 | 5/2004 | Cully et al. |
| 2004/0093016 A1 | 5/2004 | Root et al. |
| 2004/0093059 A1 | 5/2004 | Lee et al. |
| 2004/0098022 A1 | 5/2004 | Barone |
| 2004/0098026 A1 | 5/2004 | Joergensen et al. |
| 2004/0098033 A1 | 5/2004 | Leeflang et al. |
| 2004/0098112 A1 | 5/2004 | DiMatteo et al. |
| 2004/0102719 A1 | 5/2004 | Keith et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0138696 A1 | 7/2004 | Drasler et al. |
| 2004/0153117 A1 | 8/2004 | Clubb et al. |
| 2004/0153118 A1 | 8/2004 | Clubb et al. |
| 2004/0158278 A1 | 8/2004 | Becker et al. |
| 2004/0162576 A1 | 8/2004 | Barbut et al. |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0199203 A1 | 10/2004 | Oslund et al. |
| 2004/0204737 A1 | 10/2004 | Boismier et al. |
| 2004/0215322 A1 | 10/2004 | Kerr |
| 2004/0225321 A1 | 11/2004 | Krolik et al. |
| 2004/0236369 A1 | 11/2004 | Dubrul |
| 2005/0004663 A1 | 1/2005 | Llanos et al. |
| 2005/0027345 A1 | 2/2005 | Horan et al. |
| 2005/0038468 A1 | 2/2005 | Panetta et al. |
| 2005/0038503 A1 | 2/2005 | Greenhaigh |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009790 A1 | 1/2006 | Kleshinski et al. |
| 2006/0009798 A1 | 1/2006 | Callister et al. |
| 2006/0020334 A1 | 1/2006 | Lashinski et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0184194 A1 | 8/2006 | Pal et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287668 A1 | 12/2006 | Fawzi et al. |
| 2007/0038241 A1 | 2/2007 | Pal |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0167974 A1 | 7/2007 | Cully et al. |
| 2007/0185521 A1 | 8/2007 | Bui et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1* | 5/2008 | Steingisser et al. .......... 606/200 |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1127556 A2 | 8/2001 |
| EP | 1310219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/08743 | 2/2001 |
| WO | WO 01/45590 | 6/2001 |
| WO | WO 01/82831 | 11/2001 |
| WO | WO 03/077799 A2 | 9/2003 |
| WO | WO 2006/138391 A2 | 12/2006 |

OTHER PUBLICATIONS

Rubicon Embolic Filter, The Next Generation of EM, Rubicon Medical, www.rubiconmed.com.

Heeschen et al., Nature Medicine 7 (2001), No. 7, pp. 833-839.

Johnson et al., Circulation Research 94 (2004), No. 2, pp. 262-268.

International Search Report and Written Opinion for PCT/US2007/020300.

Brochure, "Shuttle Select™ System for Carotid Artery Access," (2004), pp. 1-3.

Brochure, "Slip-Cath® Angiographic Selective Catheters," (2004), pp. 1-6.

Finol, E.A. et al., "Performance Assessment of Embolic Protection Filters for Carotid Artery Stenting," *Modelling in Medicine and Biology IV*, (2005), vol. 8, pp. 133.

\* cited by examiner

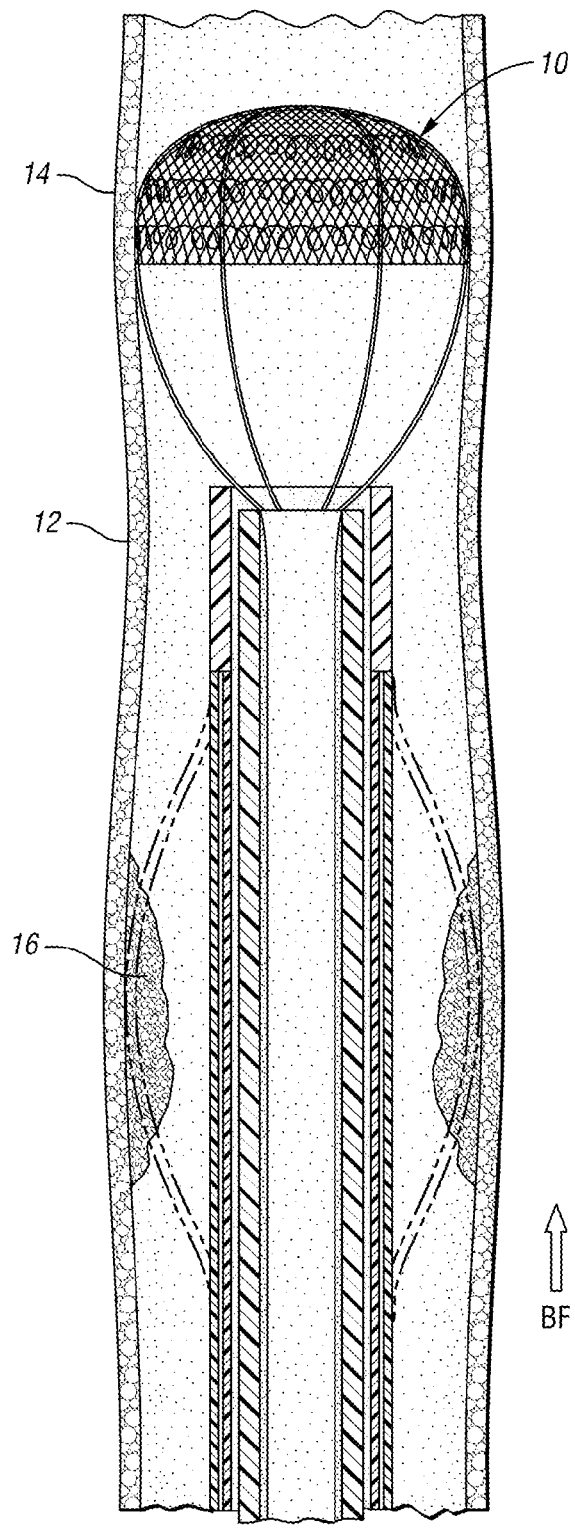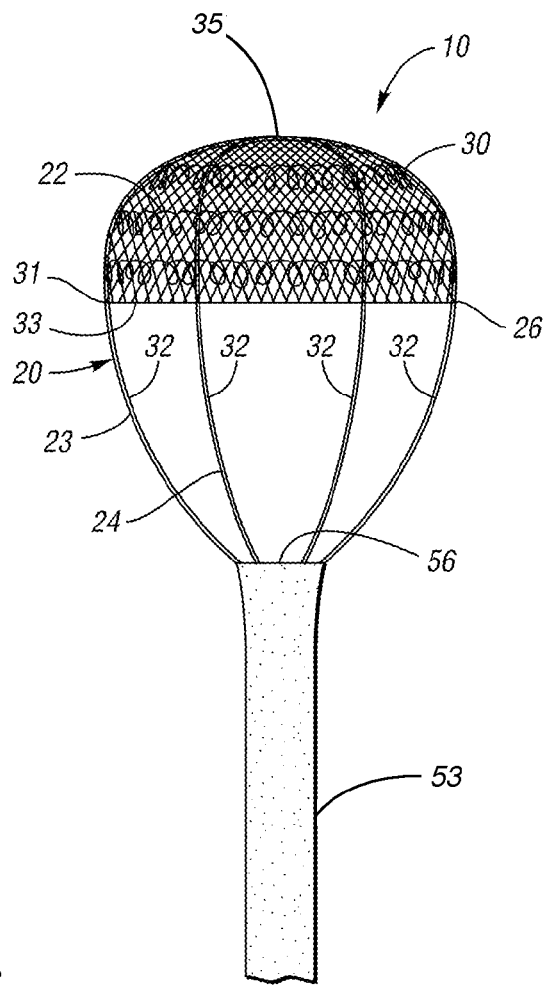
Fig. 1
Fig. 2

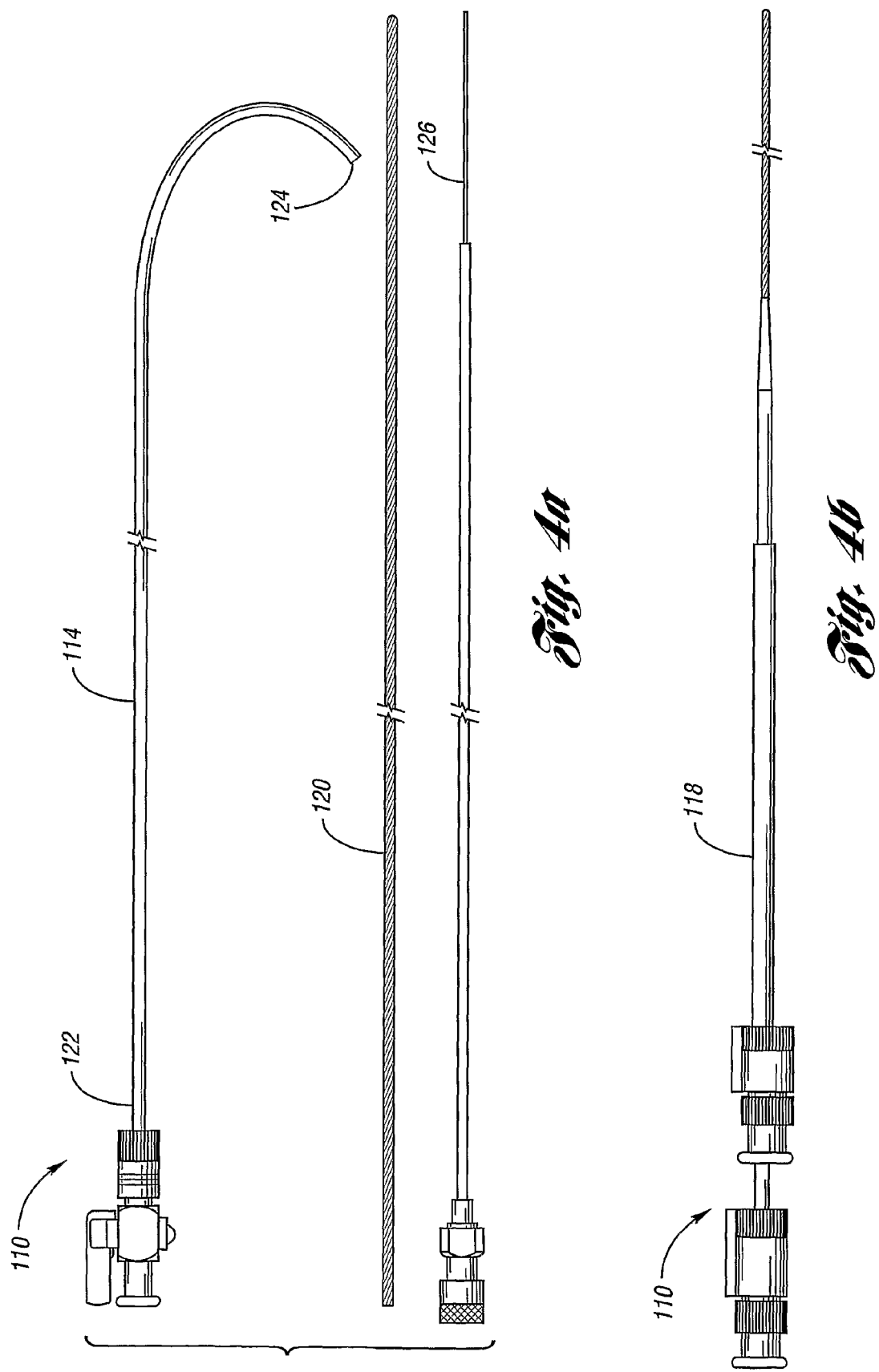

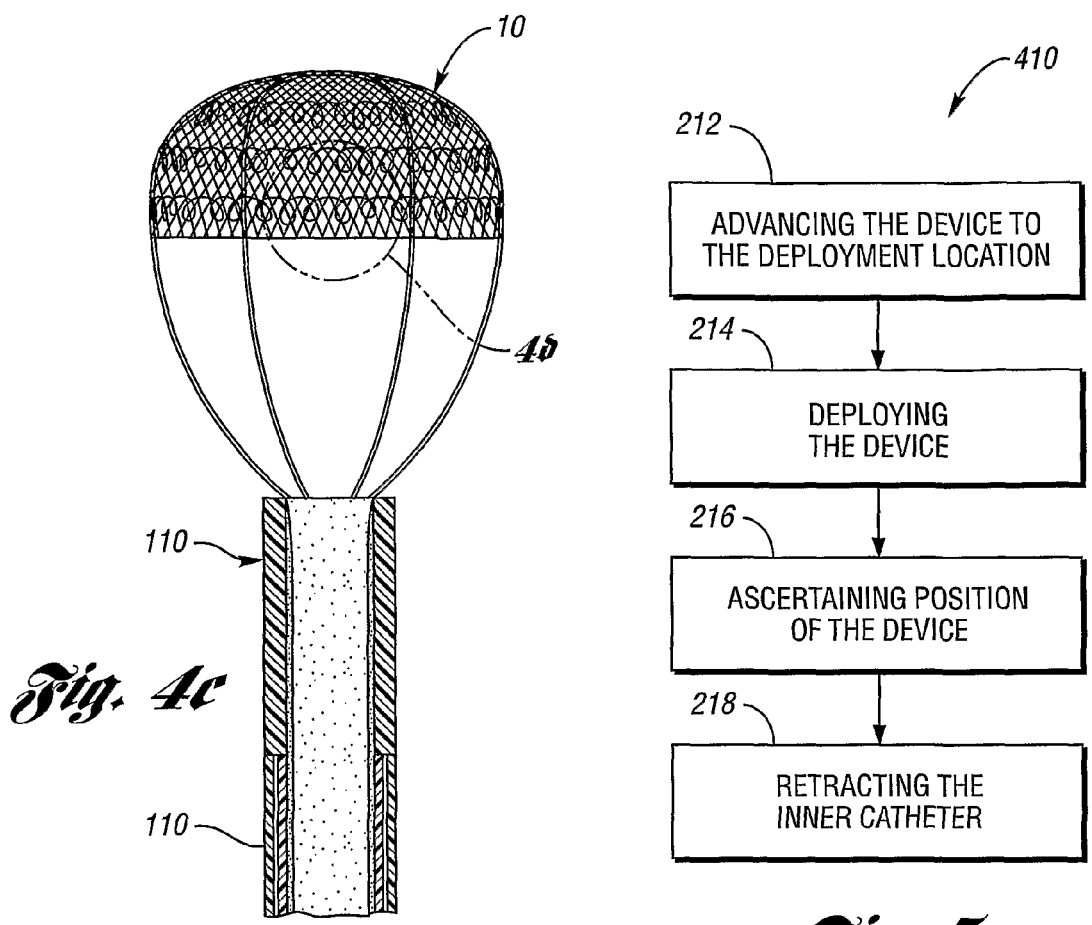
Fig. 4c
ADVANCING THE DEVICE TO THE DEPLOYMENT LOCATION — 212
DEPLOYING THE DEVICE — 214
ASCERTAINING POSITION OF THE DEVICE — 216
RETRACTING THE INNER CATHETER — 218
Fig. 5
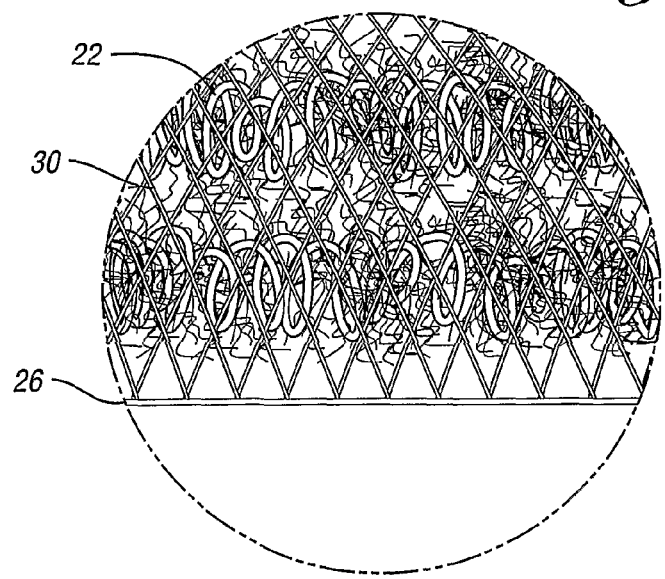
Fig. 4b

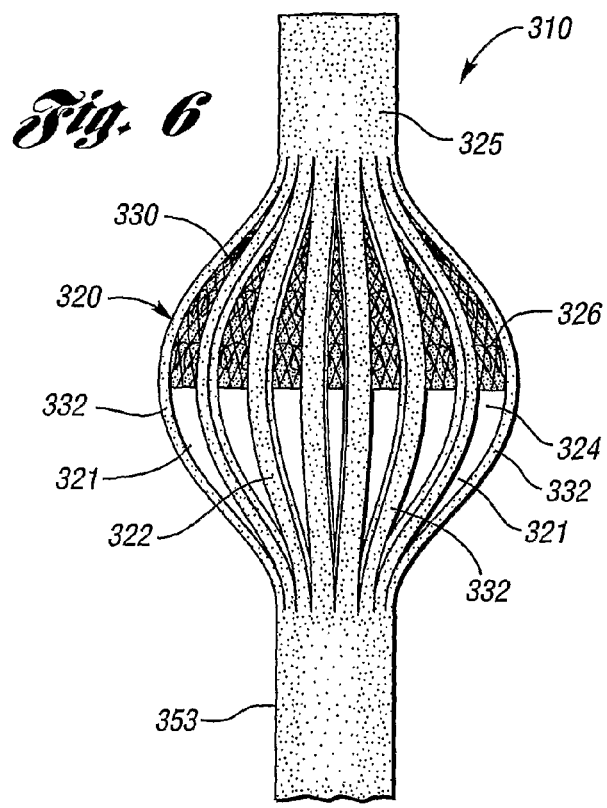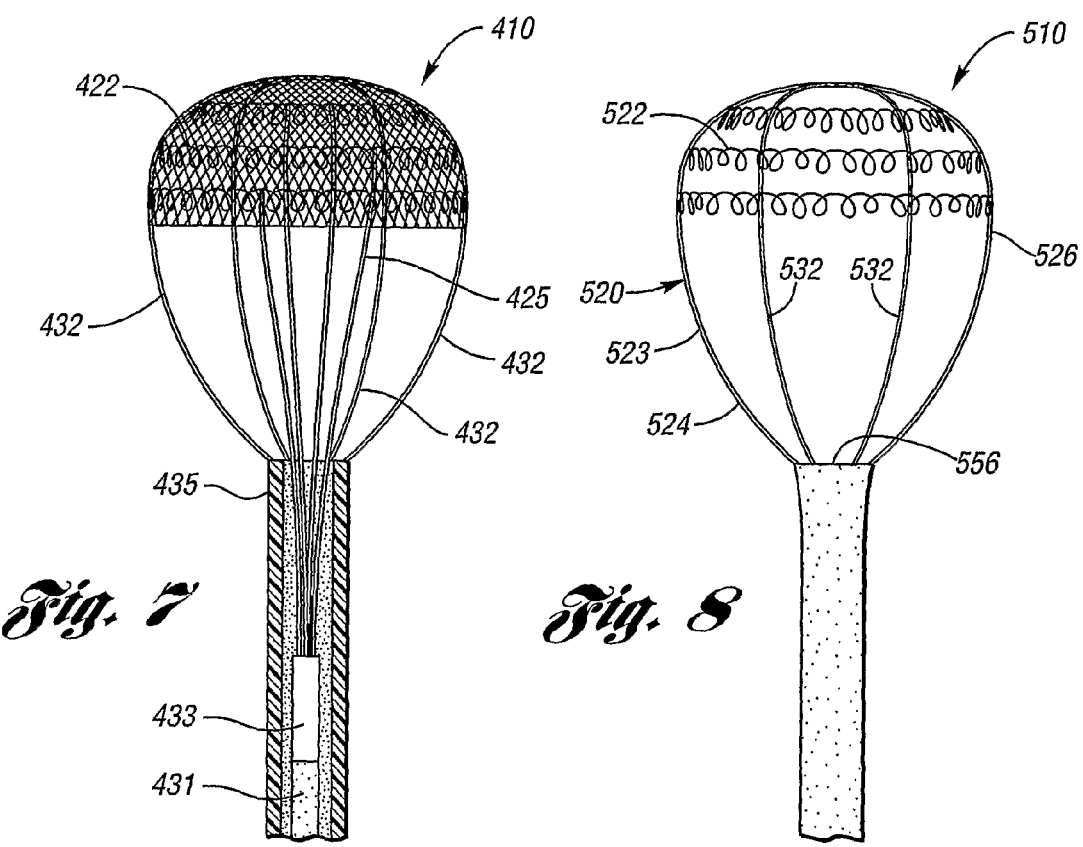

EMBOLI CAPTURING DEVICE HAVING A COIL AND METHOD FOR CAPTURING EMBOLI

CROSS-REFERENCE TO RELATED APPLICATIONS

This application claims the benefit of U.S. Provisional Application Ser. No. 60/616,577, filed on Oct. 6, 2004, entitled "EMBOLI CAPTURING DEVICE AND METHOD FOR CAPTURING EMBOLI," the entire contents of which are incorporated herein by reference.

BACKGROUND OF THE INVENTION

The present invention relates to medical devices. More particularly, the present invention relates to emboli capturing devices and methods for capturing emboli within a body vessel.

Distal protection devices that are percutaneously placed in a body vessel have been available for years. Currently, there are a number of approaches for distal protection to prevent emboli from traveling to create an undesirable embolism, e.g., pulmonary embolism. For example, vena cava filters are more commonly being used for trapping emboli in the vena cava filter to prevent pulmonary embolism. Also, anti-platelet agents and anticoagulants may be used to breakdown blood clots. Moreover, snares and baskets (e.g., stone retrieval baskets) are more commonly used for retrieving urinary calculi. Additionally, coils are commonly used to occlude aneurysms and accumulate thrombi in a body vessel.

Treatments for a stenotic lesion provide a potential in releasing blood clots and other thrombi plaque in the vasculature of the patient. One example is the treatment for a carotid artery stenosis. Generally, carotid artery stenosis is the narrowing of the carotid arteries, the main arteries in the neck that supply blood to the brain. Carotid artery stenosis (also called carotid artery disease) is a relatively high risk factor for ischemic stroke. The narrowing is usually caused by plaque build-up in the carotid artery. Plaque forms when cholesterol, fat and other substances form in the inner lining of an artery. This formation process is called atherosclerosis.

Depending on the degree of stenosis and the patient's overall condition, carotid artery stenosis has been treated with surgery. The procedure (with its inherent risks) is called carotid endarterectomy, which removes the plaque from the arterial walls. Carotid endarterectomy has proven to benefit patients with arteries substantially narrowed, e.g., by about 70% or more. For people with less narrowed arteries, e.g., less than about 50%, an anti-clotting drug may be prescribed to reduce the risk of ischemic stroke. Examples of these drugs are anti-platelet agents and anticoagulants.

Carotid angioplasty is a more recently developed treatment for carotid artery stenosis. This treatment uses balloons and/or stents to open a narrowed artery. Carotid angioplasty is a procedure that can be performed via a standard percutaneous transfemoral approach with the patient anesthetized using light intravenous sedation. At the stenosis area, an angioplasty balloon is delivered to predilate the stenosis in preparation for stent placement. The balloon may then be removed and exchanged via catheter for a stent delivery device. Once in position, a stent may then be deployed across the stenotic area. If needed, an additional balloon can be placed inside the deployed stent for post-dilation to make sure the struts of the stent are pressed firmly against the inner surface of the vessel wall. During the stenosis procedure however, there is a risk of such blood clots and thrombi being undesirably released into the blood flow within the vasculature.

Thus, there is a need to provide a device and method for distally protecting and capturing emboli within a body lumen during a stenosis procedure.

BRIEF SUMMARY OF THE INVENTION

In one embodiment, the present invention provides an embolic capturing device for capturing emboli within a body lumen. The device comprises a basket including a frame and a filtering body disposed on the frame configured to have an expanded state and a collapsed state. The frame has first and second portions. The filtering body has a lip disposed on the second portion of the frame to define an opening of the filtering body when the basket is in the expanded state for capturing emboli. The filtering body extends from the lip to a filter end. The device further comprises at least one coil attached to one of the basket and the filtering body for filtering emboli in a body lumen.

Another embodiment of the present invention provides an embolic capturing apparatus for capturing emboli within a body vessel. In this embodiment, the apparatus comprises the embolic capturing device including a tubular shaft having proximal and distal ends. The distal end of the tubular shaft is connected to the first portion of the frame. The apparatus further comprises an inner catheter in which the device is disposed for deployment in the body vessel, and an introducer sheath through which the inner catheter is advanced for percutaneous insertion into the body vessel. The introducer sheath is configured to allow the inner catheter to be disposed therethrough for positioning of the device in the body vessel. The apparatus further comprises an outer catheter co-axially disposed about the inner catheter and within the introducer sheath to collapse and expand the embolic capturing device for delivery and retrieval thereof.

Yet another embodiment of the present invention is a method for capturing emboli within a body vessel. The method comprises percutaneously introducing the embolic capturing device for capturing emboli during a stenosis procedure at a stenotic area, and disposing the embolic capturing device through the stenotic area. The method further comprises deploying the embolic capturing device in the body vessel downstream of the stenotic area to capture emboli during the stenosis procedure.

Further objects, features, and advantages of the present invention will become apparent from consideration of the following description and the appended claims when taken in connection with the accompanying drawings.

BRIEF DESCRIPTION OF THE DRAWINGS

FIG. 1 is a side environmental view of an embolic capturing device disposed in a body vessel during a stenosis procedure in accordance with one embodiment of the present invention;

FIG. 2 is a side view of the embolic capturing device of FIG. 1;

FIG. 4a is an exploded view of an embolic capturing apparatus for capturing emboli in a body vessel in accordance with one embodiment of the present invention;

FIG. 4b is a side view of the embolic capturing apparatus in FIG. 4a;

FIG. 4c is a break-away side view of the device of the distal protection apparatus for delivery from a balloon angioplasty catheter;

FIG. 4d is an enlarged view of the device in FIG. 4c in circle 4d;

FIG. 5 is a flow chart depicting one method of capturing emboli in a body vessel caused by a stenosis procedure.

FIG. 6 is a side view of an embolic capturing device in accordance with another embodiment of the present invention;

FIG. 7 is a side view of an embolic capturing device in accordance with yet another embodiment of the present invention; and FIG. 8 is a side view of an embolic capturing device in accordance with another embodiment of the present invention.

DETAILED DESCRIPTION OF THE INVENTION

Figure 3A:
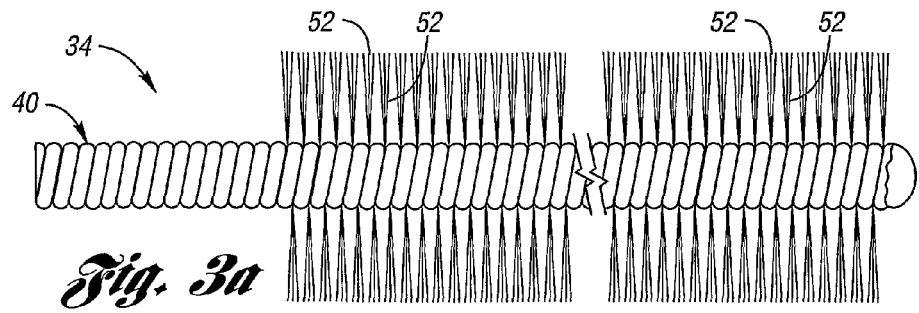
FIG. 3a is a side view of a primary coil body of one of the coils in FIG. 2.
Figure 3B:
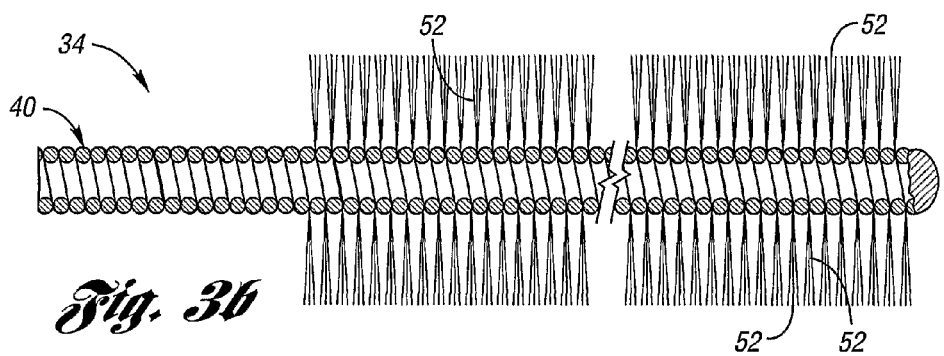
FIG. 3b is a cross sectional view of the primary coil body in FIG. 2b taken along line 3b-3b.

Embodiments of the present invention generally provide embolic capturing devices, embolic capturing apparatus, and methods for capturing emboli in a body vessel during angioplasty for treatment of a stenosis. One particular stenosis is a carotid artery stenosis. The embodiments solve the concerns of current stenosis treatments, such as the relatively high risks of surgery and the potential release of emboli into the vasculature during the stenosis procedure. Embodiments of the present invention provide a relatively low risk approach to capturing emboli released during a stenosis procedure, e.g., balloon angioplasty.

FIG. 1 illustrates an embolic capturing device 10 percutaneously deployed in a body vessel 12, e.g., the carotid artery, of a patient during balloon angioplasty or vascular stenting. As shown, device 10 is percutaneously deployed at a deployment location 14 downstream from a stenotic area 16 in the body vessel 12. For example, device 10 may be used during a percutaneous transluminal coronary angioplasty at the carotid artery. As shown, the stenotic area 16 is an area in the body vessel 12 whereat a relatively large amount of plaque build-up has occurred. As known, a common treatable cause of acute stroke is atheromatous narrowing at the carotid artery. It is generally believed that in this situation ischemic stroke commonly occurs from local thrombus formation that develops as a consequence of plaque build-up, ulceration, and laminar flow disturbances in and around the stenotic area. The local thrombus formation serves as a source for eventual arterial thrombo-embolism downstream into the intracranial circulation, commonly to the middle cerebral artery territory.

The embolic capturing device 10 is configured to be compressed or collapsed in a loaded state for delivery through a catheter to a deployment location 14 within the body vessel 12. At the deployment location 14, the embolic capturing device 10 is configured to be deployed and expanded in an expanded state within the body vessel 12. As mentioned in greater detail below, embodiments of a delivery apparatus are configured to dispose the embolic capturing device 10 at the deployment location 14 downstream from the stenotic area 16 to capture emboli.

FIG. 2 depicts the embolic capturing device 10 for capturing emboli in a body vessel 12 for a stenosis procedure in accordance with one embodiment of the present invention. As shown, embolic capturing device 10 comprises a basket 20 and at least one coil 22 attached to the basket 20 for capturing emboli in the body vessel 12. In this embodiment, the basket 20 includes a frame 23 having first and second portions 24 and 26. The basket 20 further includes a filtering body 30 disposed on the frame 23. In this embodiment, the first portion 24 is a proximal portion and the second portion 26 is a distal portion of the frame 23. As shown, the frame 23 is defined by a plurality of struts 32 extending from the first portion 24 to the second portion 26. In this embodiment, the struts 32 extend from the first portion 24 to the second portion 26. The struts may be attached to the distal end 56 of the tubular shaft or may extend proximally to the proximal end of the delivery apparatus.

Preferably, the filtering body 30 is disposed on the second portion 26 of the frame 23, which is configured to have an expanded state and a collapsed state. As shown, the filtering body 30 has a lip 31 disposed on the second portion 26 of the basket 20 to define an opening 33 of the filtering body 30 when the basket 20 is in the expanded state for capturing emboli. The filtering body 30 extends from the lip 31 to a filter end 35.

The filtering body 30 is preferably a woven mesh or net configuration disposed on the frame 23. However, the filtering body 30 may be any other suitable filtering mechanism such as a filtering membrane without falling beyond the scope of spirit of the present invention. The filtering body 30 may be made of any suitable material, such as super-elastic material (e.g. Nitinol), connective tissue material, shape memory alloy, aluminum, platinum, metal alloy, mesh/net cloth, nylon, polymeric material, polytetrafluoroethylene (PTFE), or woven mixtures thereof without falling beyond the scope or spirit of the present invention.

In one embodiment, the filtering body 30 is made of connective tissue material for capturing emboli. In this embodiment, the connective tissue comprises extracellular matrix (ECM). As known, ECM is a complex structural entity surrounding and supporting cells that are found within mammalian tissues. More specifically, ECM comprises structural proteins (e.g., collagen and elastin), specialized protein (e.g., fibrillin, fibronectin, and laminin), and proteoglycans, a protein core to which are attached are long chains of repeating disaccharide units termed of glycosaminoglycans.

Most preferably, the extracellular matrix is comprised of small intestinal submucosa (SIS). As known, SIS is a resorbable, acellular, naturally occurring tissue matrix composed of ECM proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. In many aspects, SIS is used to induce site-specific remodeling of both organs and tissues depending on the site of implantation. In theory, host cells are stimulated to proliferate and differentiate into site-specific connective tissue structures, which have been shown to completely replace the SIS material in time.

In this embodiment, SIS is used to temporarily adhere the filtering body 30 to the walls of a body vessel in which the device 10 is deployed. SIS has a natural adherence or wettability to body fluids and connective cells comprising the connective tissue of a body vessel wall. Due to the temporary nature of the duration in which the device 10 is deployed in the body vessel, host cells of the wall will adhere to the filtering body 30 but not differentiate, allowing for retrieval of the device 10 from the body vessel.

The filtering body 30 may be disposed on the frame 23 by any suitable means, such as by thermal bonding, sonic welding, or adhesive bonding. Preferably, the filtering body 30 is disposed on the frame 23. In use, the filtering body 30 preferably is self-expandable such that when the frame 23 radially expands during deployment, the filtering body expands consistently with negligible resistance, if any.

In this embodiment, a plurality of coils 22 is attached to the basket 20. Preferably, each coil is attached to a strut 32 and radially extends across the basket 20 to attach to another strut 32. Preferably, a plurality of coils 22 are attached to the frame 23 for filtering emboli in the body vessel 12. The coils may be attached to the struts 32 by any suitable means such as by thermal bonding or sonic welding.

In this embodiment, the embolic capturing device 10 further comprises a tubular shaft 53 having a proximal end (not shown) and a distal end and 56. In one example, the first portion 24 of the frame 23 may be connected to the distal end 56 of the tubular shaft 53 or may proximally extend to the proximal end of the delivery apparatus. For example, the plurality of struts 32 may be bonded to the distal end of the tubular shaft 53. In another example, each of the struts 32 may distally extend from the proximal end of the tubular shaft or delivery apparatus through the distal end of the tubular shaft and curve back proximally, defining the basket, to the proximal end of the tubular shaft. As discussed below, the plurality of struts 32 may be comprised of a super-elastic material or a shape memory alloy, such as Nitinol. The struts 32 may be bonded to the distal portion of the tubular shaft 53 by any suitable means such as by thermal bonding or sonic welding.

Figure 3C:
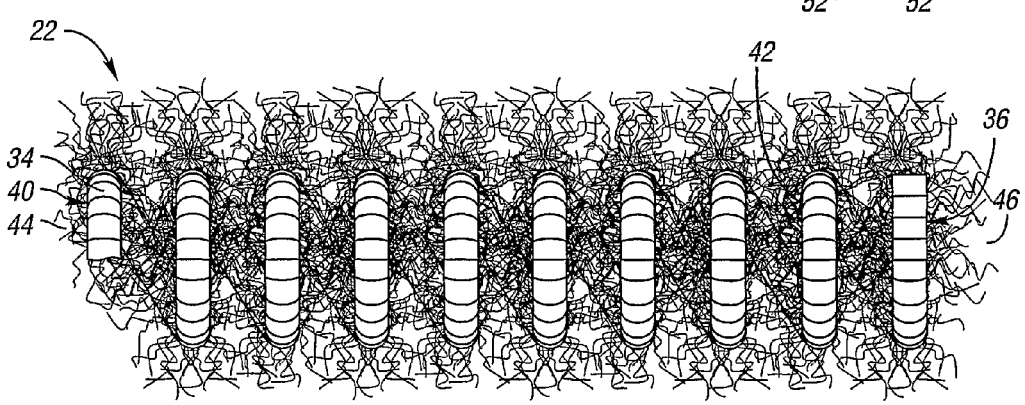
FIG. 3c is a side view of one of the coils depicting a secondary coil body.
Figure 3D:
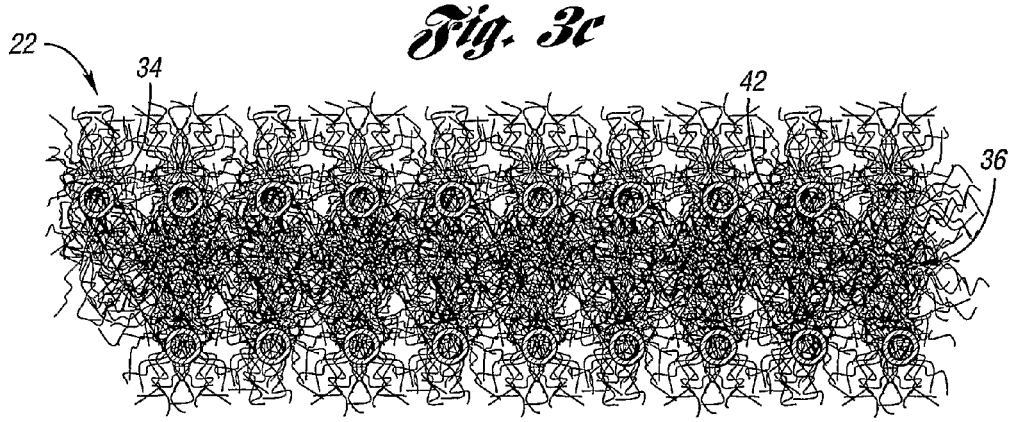
FIG. 3d is a cross sectional view of the coil of FIG. 3c taken along line 3d-3d.

In one embodiment shown in FIGS. 3a to 3d, each of the coils may comprise a primary coil body 34 formed in a secondary coil body 36. Preferably, the primary coil body 34 is formed to define a primary structure 40. As shown, the primary structure 40 is wound, preferably by a coil winding machine, to a helical shape to define the secondary coil body 36. As shown in FIGS. 3c and 3d, the secondary coil body 36 includes a series of loops 42 having a first end 44 and a second end 46. The series of loops 42 define a cross sectional lumen 50 formed axially along the coil. Preferably, each coil further includes fibers 52 attached to the primary coil body 34 by the initial tension thereof (discussed below).

Preferably, each coil is comprised of platinum or any other suitable metal, composition, or alloy having a predetermined magnitude of tensile strength, e.g., between about 40,000 and 400,000 pounds per square inch. In this embodiment, the primary coil body 34 includes a predetermined initial tension, e.g., between about 5 and 100 grams of weight. Initial tension may be defined to be the amount of force required to cause a 4 centimeter length of coil to begin to elongate. The initial tension may also be defined by the amount of force required to cause a coil to begin elongating at a ratio of between about 1.25 to 15 grams per centimeter. Moreover, each primary coil body 34 may have a length of between about 5 and 15 centimeters, and may have an outer diameter ranging between about 5 and 15 millimeters. Preferably, the strands 52 have a length extending from the coil of between about 5 to 10 millimeters and have an outer diameter of about 0.00050 to 0.00100 inch.

FIGS. 4a to 4d depict an embolic capturing apparatus 110 which implements the embolic capturing device 10 for capturing thrombi in a body vessel in accordance with one embodiment of the present invention. As shown, the apparatus 110 includes an inner catheter 114 defining a catheter lumen and preferably made of a soft, flexible material such as a silicone or any other suitable material. Generally, the inner catheter 114 has a proximal end 122, a distal end 124, and a plastic adapter or hub 116 to receive apparatus to be advanced therethrough. In this embodiment, the inside diameter of the inner catheter may range between 0.014 and 0.027 inch. The apparatus 110 further includes a wire guide 120 which provides an introducer sheath 118 (discussed in greater detail below) a path during insertion of the introducer sheath 118 within a body vessel. The size of the wire guide is based on the inside diameter of the introducer sheath.

As mentioned above, the apparatus 110 further includes a polytetrafluoroethylene (PTFE) introducer sheath 118 for percutaneously introducing the inner catheter 114 in a body vessel. Of course, any other suitable material may be used without falling beyond the scope or spirit of the present invention. The sheath 118 may have a size of about 4-French to 8-French and allows the inner catheter 114 to be inserted therethrough to the deployment location in the body vessel. The sheath 118 receives the inner catheter 114 and provides stability of the inner catheter 114 at the deployment location. When the distal end 124 of the inner catheter 114 is at the deployment location in the body vessel, the tubular shaft and the capturing device are advanced through the inner catheter and the device is deployed through the distal end 124.

The apparatus 110 may further include an outer catheter 123 disposed co-axially about the inner catheter within the introducer sheath. The outer catheter 123 is advanced with the inner catheter 114 to the deployment location. As the device 10 is deployed through the inner catheter 114, the outer catheter facilitates deployment in the body vessel as it is restricted relative to inner catheter 114.

In one embodiment, the outer catheter may have an expandable balloon 125, as shown in FIG. 4c, disposed radially thereon to allow for balloon angioplasty and vascular stenting. During the stenosis procedure, the balloon of the outer catheter is positioned at the stenotic area via fluoroscopy. As the outer catheter is maintained its position within the vasculature, the inner catheter may be distally advanced relative to the apparatus toward the deployment location downstream from the stenotic area. Thus, during balloon angioplasty and vascular stenting, the embolic capturing device is deployed at the deployment location to capture emboli that have detached from the stenotic area.

It is to be understood that the apparatus 110 described above is merely one example of an apparatus that may be used to deploy the capturing device in a body vessel. Of course, other apparatus, assemblies, and systems may be used to deploy any embodiment of the capturing device without falling beyond the scope or spirit of the present invention.

FIG. 5 illustrates an example of one method 210 of capturing emboli within a body vessel during angioplasty. In this embodiment, the introducer sheath is percutaneously introduced into the body vessel of a patient and the outer catheter is then guided through the introducer sheath and the balloon is positioned at the stenotic area via the wire guide. The embolic capturing device is compressed to its loaded state, and loaded at the proximal end of the inner catheter. The inner catheter is advanced through the outer catheter and the device is advanced to the deployment location in step 212. In step 214, the device is deployed at the deployment location in the body vessel. This may be accomplished by maintaining the position of the outer catheter such that the balloon maintain their position at the stenotic area while advancing the inner catheter to the deployment location downstream from the stenotic area. As a result, the basket will deploy and expand the device within the body vessel.

In step 216, the location of the device in the body vessel is ascertained by any suitable means, such as by fluoroscopy. If the device is at the deployment location in the body vessel, then the inner catheter is retracted therefrom in step 218. Preferably, the device is deployed by moving the distal end of the inner catheter along the lumen of the body vessel.

FIG. 6 illustrates an embolic capturing device 310 in accordance with another embodiment of the present invention. In the example shown in FIG. 6, the plurality of struts 332 of the basket 320 may be formed integrally with the tubular shaft. For example, the basket 320 may be formed of a malecot configuration, wherein the tubular shaft 353 has slits 321 longitudinally formed thereon defining the frame 323. In this embodiment, the tubular shaft has a shaft body extending to a distal portion 325 thereof. As shown, the second portion 326 of the frame is integral with the distal portion 325 of the frame and the first portion 324 is integral with the shaft body 355 to define the malecot configuration.

Upon axial pressure to the malecot configuration, the struts 332 (defined by the slits 321) radially expand to form the basket 320 for capturing emboli. In this embodiment, the filtering body is disposed on the frame 323 and is self-expandable so that when the frame 323 expands, the filtering body expands consistently as well with negligible resistance, if any. The malecot configuration provides a more simplified deployment and a retrieval of the basket 320 from the body vessel. In this embodiment, the struts 332, basket 320, and tubular shaft 353 are made of a PTFE.

FIG. 7 depicts an embolic capturing device 410 in accordance with yet another embodiment of the present invention. As shown, the device 410 includes a plurality of struts 432, each strut 432 being an elongate member attached proximally to a hub 433 of a push wire 431. In this embodiment, the struts 432 and push wire 431 are configured to be passed through an inner catheter 435 of a delivery apparatus. The push wire 431 allows for the struts 432 to be deployed and retrieved from the body vessel by pushing or retracting the embolic capturing device 410 relative to the delivery apparatus.

In this embodiment, each of the coils 422 includes a tether 425 proximally extending therefrom to provide for an easier and simplified way of retrieving the coils 422 from deployment. In this embodiment, each tether 425 proximally extends from the basket through the catheter lumen to a common joint for delivery and retrieval. A practitioner is able to retrieve and push the coil through the catheter lumen from the proximal end of the push wire.

The struts mentioned above, e.g. struts 32 of FIGS. 1 and 2, may be comprised of any suitable material such as a super-elastic material, stainless steel wire, cobalt-chromium-nickel-molybdenum-iron alloy, or cobalt-chrome alloy. It is understood that the struts may be formed of any other suitable material that will result in a self-opening or self-expanding basket, such as shape memory alloys. Super-elastic, shape memory alloys have a property of becoming rigid, that is, returning to a remembered state, when heated above a transition temperature. A shape memory alloy suitable for the present invention may comprise Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one alternate embodiment, the struts, e.g., the struts 32 of FIGS. 1 and 2, may be made from Nitinol with a transition temperature that is slightly below normal body temperature of humans, which is about 98.6° F. Although not necessarily a preferred embodiment, when the struts 32 is deployed in a body vessel and exposed to normal body temperature, the alloy of the struts 32 will transform to austenite, that is, the remembered state, which for one embodiment of the present invention is the expanded configuration when the struts 32 is deployed in the body vessel. To remove the basket, the struts 32 are cooled to transform the material to martensite which is more ductile than austenite, making the struts 32 more malleable. As such, the basket can be more easily collapsed and pulled into a lumen of a catheter for removal.

In another alternate embodiment, the struts 32 may be made from Nitinol with a transition temperature that is above normal body temperature of humans, which is about 98.6° F. Although not necessarily a preferred embodiment, when the struts 32 is deployed in a body vessel and exposed to normal body temperature, the struts 32 is in the martensitic state so that the struts 32 is sufficiently ductile to bend or form into a desired shape, which for the present invention is an expanded configuration. To remove the basket, the struts 32 are heated to transform the alloy to austenite so that the struts 32 becomes rigid and returns to a remembered state, which for the struts 32 in a collapsed configuration.

FIG. 8 depicts the embolic capturing device 510 for capturing emboli in a body vessel for an endoluminal procedure in accordance with another embodiment of the present invention. As shown, embolic capturing device 510 comprises a basket 520 and at least one coil 522 attached to the basket 520 for capturing emboli in a body vessel. In this embodiment, the basket 520 includes a frame 523 having first and second portions 524 and 526. In this embodiment, the first portion 524 is a proximal portion and the second portion 526 is a distal portion of the frame 523. As shown, the frame 523 is defined by a plurality of struts 532 extending from the first portion 524 to the second portion 526. In this embodiment, the struts 532 extend from the first portion 524 to the second portion 526. The struts 523 preferably extend proximally to the proximal end of the delivery apparatus. The struts may be attached to the distal end 556 of the tubular shaft or may extend proximally to the proximal end of the delivery apparatus.

While the present invention has been described in terms of preferred embodiments, it will be understood, of course, that the invention is not limited thereto since modifications may be made to those skilled in the art, particularly in light of the foregoing teachings.

The invention claimed is:

1. An embolic capturing device for capturing emboli within a lumen, the device comprising:
    a basket including a frame and a filtering body disposed on said frame, the basket being configured to have an expanded state and a collapsed state, the filtering body defining a filter volume when the basket is in the expanded state, the frame comprising a plurality of struts; and
    at least one coil separate from the filtering body and having a helical winding, the at least one coil attached to one strut of the basket, the at least one coil fixedly extending radially across the basket and across the filter volume from one strut to another strut and fixedly attached to the another strut for capturing emboli when the basket is in the expanded state.

2. The device of claim 1 further comprising the frame having first and second portions, the filtering body having a lip disposed on the second portion of the frame to define an opening of the filtering body when the basket is in the expanded state for capturing emboli, the filtering body extending from the lip to a filter end.

3. The device of claim 2 wherein the filtering body is disposed on the second portion of the frame.

4. The device of claim 1 wherein the at least one coil comprises a plurality of coils.

5. The device of claim 1 further comprising a tubular shaft having a shaft body extending to a distal portion, the shaft body having slits formed longitudinally therethrough to the distal portion, the slits defining said plurality of struts forming the frame of the basket.

6. The device of claim 5 wherein the tubular shaft is formed of a malecot configuration, the second portion of the frame being integral with the distal portion and the first portion being integral with the shaft body to define the malecot configuration.

7. The device of claim 2 further comprising a tubular shaft having proximal and distal ends, the distal end being connected to the first portion of the frame for delivery and retrieval of the device.

8. The device of claim 7 further comprising the plurality of struts including at least one pair of opposed struts being integrally formed, each pair of struts being configured to distally extend from the proximal end of the tubular shaft to the second portion and further extend oppositely to the proximal end, defining the basket.

9. The device of claim 1 further comprising a filtering body of super-elastic material, connective tissue material, shape memory alloy, aluminum, platinum, metal alloy, nylon, polymeric material, polytetrafluoroethylene, or a mixture thereof.

10. The device of claim 1 wherein the struts are formed of a super-elastic material or a shape memory alloy.

11. The apparatus of claim 7 wherein the tubular shaft further includes a balloon formed thereon for stenosis procedure.

12. A method for capturing emboli within a body vessel, the method comprising:
percutaneously introducing an embolic capturing device for capturing emboli during a stenosis procedure at a stenotic area, the embolic capturing device including:
a basket including a frame and a filtering body attached within the frame, the filtering body defining a filter volume, the frame having first and second portions; and
at least one coil having a helical winding, the at least one coil fixedly attached to one strut of the basket and extending radially across the basket and across the filter volume to another strut and fixedly attached to the another strut for filtering emboli in a body lumen;
disposing the embolic capturing device through the stenotic area; and
deploying the embolic capturing device in the body vessel to capture emboli.

13. An embolic capturing device for capturing emboli within a lumen, the device comprising:
a basket including a frame and a filtering body disposed on said frame, the basket being configured to have an expanded state and a collapsed state, the filtering body defining a filter volume when the basket is in the expanded state, the frame comprising a plurality of struts; and
at least one coil separate from the filtering body and wound into a primary coil body having a first helical winding, the primary coil body further wound into a secondary coil body having a second helical winding, the at least one coil fixedly attached to one strut of the basket, the at least one coil extending radially across the basket and across the filter volume from one strut to another strut and fixedly attached to the another strut for capturing emboli when the basket is in the expanded state.

14. The device of claim 13 further comprising the frame having first and second portions, the filtering body having a lip disposed on the second portion of the frame to define an opening of the filtering body when the basket is in the expanded state for capturing emboli, the filtering body extending from the lip to a filter end.

15. The device of claim 14 wherein the filtering body is disposed on the second portion of the frame.

16. The device of claim 13 further comprising a tubular shaft having a shaft body extending to a distal portion, the shaft body having slits formed longitudinally therethrough to the distal portion, the slits defining said plurality of struts forming the frame of the basket.

17. The device of claim 16 wherein the tubular shaft is formed of a malecot configuration, the second portion of the frame being integral with the distal portion and the first portion being integral with the shaft body to define the malecot configuration.

18. The device of claim 14 further comprising a tubular shaft having proximal and distal ends, the distal end being connected to the first portion of the frame for delivery and retrieval of the device.

19. The device of claim 18 further comprising the plurality of struts including at least one pair of opposed struts being integrally formed, each pair of struts being configured to distally extend from the proximal end of the tubular shaft to the second portion and further extend oppositely to the proximal end, defining the basket.

20. The device of claim 13 further comprising a filtering body of super-elastic material, connective tissue material, shape memory alloy, aluminum, platinum, metal alloy, nylon, polymeric material, polytetrafluoroethylene, or a mixture thereof.

* * * * *

UNITED STATES PATENT AND TRADEMARK OFFICE
CERTIFICATE OF CORRECTION

| | | |
|---|---|---|
| PATENT NO. | : 8,795,315 B2 | Page 1 of 1 |
| APPLICATION NO. | : 11/664903 | |
| DATED | : August 5, 2014 | |
| INVENTOR(S) | : Hunt | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,241 days.

Signed and Sealed this
Twelfth Day of July, 2016

Michelle K. Lee
*Director of the United States Patent and Trademark Office*